United States Patent [19]

Hamprecht et al.

[11] 4,075,004
[45] Feb. 21, 1978

[54] 2,1,3-BENZOTHIADIAZINES

[75] Inventors: Gerhard Hamprecht, Mannheim; Ulrich Schirmer, Heidelberg; Bruno Wuerzer, Limburgerhof; Guenter Retzlaff, Roemerberg, all of Germany

[73] Assignee: BASF Aktiengesellschaft, Ludwigshafen, Germany

[21] Appl. No.: 733,524

[22] Filed: Oct. 18, 1976

[30] Foreign Application Priority Data

Nov. 27, 1975 Germany .............................. 2553209

[51] Int. Cl.² .................... C07D 285/16; A01N 9/14
[52] U.S. Cl. ......................................... 71/91; 544/11

[58] Field of Search ........................ 260/243 R; 71/91

[56] References Cited

U.S. PATENT DOCUMENTS 3,822,257  7/1974   Hamprecht et al. ............... 260/243
3,920,641  11/1975  McKendry ........................ 260/243

Primary Examiner—John M. Ford
Attorney, Agent, or Firm—Keil, Thompson & Shurtleff

[57] ABSTRACT

New and valuable substituted 2,1,3-benzothiadiazine compounds having a herbicidal action, herbicides containing these compounds, a method of controlling the growth of unwanted plants with these compounds, and methods for their manufacture.

3 Claims, No Drawings

2,1,3-BENZOTHIADIAZINES

The present invention relates to new and valuable substituted 2,1,3-benzothiadiazine compounds having a herbicidal action, herbicides containing these compounds, a method of controlling the growth of unwanted plants with these compounds, and methods for their manufacture.

It is known that 3-isopropyl-2,1,3-benzothiadiazin-(4)-one-2,2-dioxide has a herbicidal action (German Pat. No. 1,542,836-Bentazon) (German Laid-Open Applications DOS 2,444,383 and DOS 2,443,901). It is further known that substances from this class of compounds may be used for selective control of unwanted plants in cotton. Furthermore, other herbicides from this class of compounds are known (German Laid-Open Application DOS 2,355,113). There are considerable gaps in the action of all these known compounds on the various weeds. Either the compounds are not selective in numerous crops, or this selectivity is most dubious.

We have now found that compounds of the formula

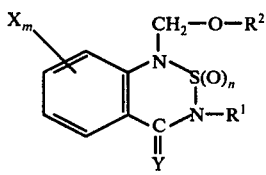   V.

where $R^1$ and $R^2$ are identical or different and each denotes hydrogen, alkyl, haloalkyl, cycloalkyl, alkenyl, alkynyl, haloalkenyl, haoalkynyl, alkoxyalkyl, alkymercaptoalkyl, alkylcarbamoylalkyl, dialkylcarbamoylalkyl, alkoxycarboalkyl, alkoxycarboalkenyl, alkylketone and benzyl, and $R^1$ additionally denotes halogen-substituted or methyl-substituted aryl, $R^1$ and $R^2$ not simultaneously denoting hydrogen, each X independently denotes halogen, $NO_2$, lower alkyl, halo lower alkyl, cycloalkyl, aryl, SCN, $CO_2R^3$,

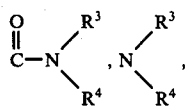

$NH_2$, $Y''R^4$, $SO_2R^3$, $SO_2OR^3$,

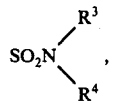

$CCl_3$, $CF_3$,

or $Y'CF_2C(Z)_3$, m denotes one of the integers 0, 1, 2, 3 and 4, and n denotes one of the integers 1 and 2, $R^3$ denoting lower alkyl, $R^4$ denoting lower alkyl or hydrogen, each Y, Y' and Y'' independently denoting oxygen or sulfur, and each Z independently denoting hydrogen, fluoro, bromo or chloro, make it possible to chemically remove unwanted dicotyledonous weeds and some important representatives of the monocotyledons from various broadleaved crop plants with a far lesser risk for the crop than is the case with prior art compounds from this class.

The new benzothiadiazine compounds are obtained by reacting 2,1,3-benzothiadiazine compounds of the formula

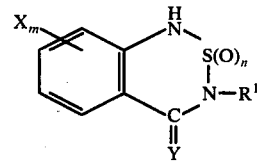   I, where $R^1$, Y, X, m and n have the above meanings, with an α-halo ether of the formula $$Hal-CH_2-O-R^2 \qquad II,$$

where $R^2$ has the above meanings and Hal denotes a halogen atom, this reaction optionally being carried out in the presence of an acid binder and optionally in the presence of a solvent; by reacting the salts of compounds of formula I with an α-halo ether of the formula II optionally in the presence of a solvent; or by reacting benzothiadiazine compounds of the formula

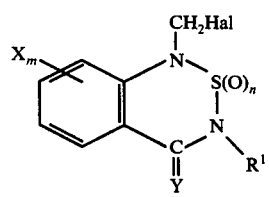   III, where $R^1$, Y, X, m and n have the above meanings and Hal denotes a halogen atom, with a hydroxy compound of the formula $$R^2OH \qquad IV,$$

where $R^2$ has the above meanings, in the presence or absence of a solvent and of an acid binder.

Examples of meanings for $R^1$ and $R^2$ are: hydrogen, methyl, ethyl, n-propyl, isopropyl, cyclopropyl, n-butyl, isobutyl, tert-butyl, cyclobutyl, n-pentyl, 2-pentyl, 3-pentyl, tert-amyl, neopentyl, 2-methylbutyl, 3-methylbutyl, 3-methyl-2-butyl, cyclopentyl, n-hexyl, 4-methyl-2-pentyl, 2,3-dimethylbutyl, 2-methyl-1-pentyl, 2-hexyl, 3-hexyl, 3-methyl-2-pentyl, 3-methylpentyl, 4-methylpentyl, 3-methyl-3-pentyl, 4,4-dimethylbutyl, cyclohexyl, heptyl, 2-heptyl, 3-heptyl, 4-heptyl, cycloheptyl, 1-octyl, 2-octyl, 3-octyl, 4-octyl, 5-octyl, 5-ethyl-2-heptyl, 2,6-dimethyl-4-heptyl, 7-ethyl-2-methyl-4-nonyl, 2,4-dimethyl-3-pentyl, 3-methyl-2-heptyl, 5-ethyl-2-nonyl, nonyl, decyl, undecyl, dodecyl, tridecyl, tetradecyl, pentadecyl, hexadecyl, heptadecyl, octadecyl, nonadecyl, eicosyl, 6-ethyl-3-decyl, 6-ethyl-3-octyl, 2-methyl-2-pentyl, 2,3-dimethyl-2-butyl, 2-methyl-2-hexyl, 3-ethyl-3-pentyl, 3-methyl-3-hexyl, 2,3-dimethylpentyl-3, 2, 4-dimethyl-2-pentyl, 2,2,3-trimethyl-3-butyl, 2-methyl-2-heptyl, 4-methyl-4-heptyl, 2,4-dimethyl-2-hexyl, 2-methyl-2-octyl, 1-methyl-1-cyclopentyl, 1-methyl-1-cyclohexyl, 1-ethyl-1-cyclohexyl, chloro-tert-butyl, 1,1-dichloro-2-methyl-2-propyl, 1,3-dichloro-2-methyl-2-propyl, 1-cyclohexyl-1-ethyl, 1-chlorooctyl, 2-chloroethyl, 1-chloropropyl, 2-chloropropyl, 3-chloropropyl, 1-chloro-2-propyl, 2-chlorobutyl, 2-chloro-2-methyl-3-propyl, 1-fluoroethyl, 2-fluoroethyl, 2-fluoropropyl, 3-fluoropropyl, 1-fluoro-2-propyl, 2-fluorobutyl, 2-fluoro-2-methyl-3-propyl, 2-bromoethyl, 3-bromopropyl, 4-chlorobutyl, 2-chlorocyclohexyl, 1,1,1-trifluoroisopropyl, hexafluoro-2-methylisopropyl, hexafluoroisopropyl, hexachloroisopropyl, 1,2-dibromoallyl, 2,2,2-trifluoroethyl, 1-chlorobutyn-2-yl-4, 3-chlorobutyn-1-yl-4, 1-chlorobuten-2-yl-4, 2,3-dibromo-1-propyl, 2,2,2-trichloroethyl, 1-chloropentyn-2-yl-4, 2,2,2-tribromoethyl, 3,4,4-trichlorobuten-3-yl-2, 1-bromo-2-propyl, 1,3-dibromo-2-propyl, 3-chlorobuten-1-yl-4, allyl, methallyl, crotyl, 2-ethylhexen-2-yl-1, hexen-5-yl-1, undecen-10-yl-1, 2-methylbuten-2-yl-1, 2-methylbuten-1-yl-3, butyn-1-yl-3, butyn-2-y-1, buten-1-yl-3, propargyl, 2-methylbuten-1-yl-4, 2-methylbuten-2-yl-4, 3-methylbuten-1-yl-3, 1-ethynylcyclohexyl, methoxyethyl, ethoxyethyl, 3-methoxypropyl, methoxyisopropyl, 3-methoxybutyl, 1-methoxybutyl-2,ethoxy-tert-butyl, methoxy-tert-butyl, cyclohexoxy-tert-butyl, 2-methoxybutyl, 4-methoxybutyl, methylmercaptoethyl, ethylmercaptoethyl, 3-methylmercaptopropyl, 3-methylmercaptobutyl, 1-methylmercaptobutyl-2, methylmercapto-tert-butyl, 2-methylmercaptobutyl, 4-methylmercaptobutyl, 3-n-butoxyethyl, 2-ethoxypropyl, 3-ethoxy-2-propyl, 2-methylbutanon-3-yl-2, 2-methylpentanon-4-yl-2, 3-butanon-1-yl, 3-butanon-2-yl, 2-propanon-1-yl, 2-pentanon-1-yl, methylacetate-2, ethylacetate-2, methylpropionate-2, methylpropionate-3, methylbutyrate-2, methylbutyrate-3, methylbutyrate-4, methyl-(2-vinyl-propionate-2), methyl -(2-vinylacetate-2), methylcarbamoylmethyl and dimethylcarbamoylmethyl.

The term "halogen" denotes fluorine, chlorine, bromine and iodine.

The terms "lower alkyl" and "halo lower alkyl" denote straight-chain or branched-chain optionally halogen-substituted alkyl of from 1 to 6 carbon atoms.

The term "cycloalkyl" denotes for instance cyclopropyl, cyclobutyl, cyclopentyl, cyclohexyl and cycloheptyl.

The term "aryl" denotes phenyl and substituted phenyl, such as halophenyl and tolyl.

If 3-ethyl-2,1,3-benzothiadiazin-(4)-one-2,2-dioxide and α-chloromethyl ether are used as starting materials, the reaction may be represented by the following formula scheme (a):

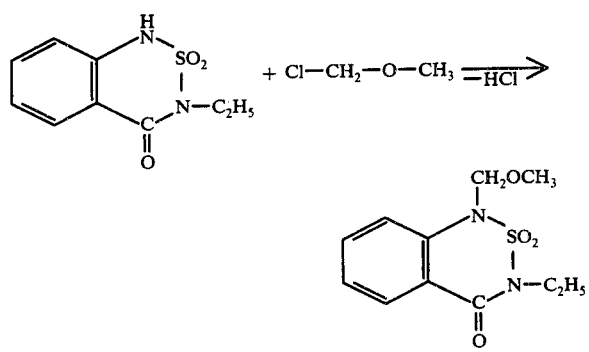

If 1-chloromethyl-3-ethyl-2,1,3-benzothiadiazin-(4)-one-2,2-dioxide and allyl alcohol are used as starting materials, the reaction may be represented by the following formula scheme (b):

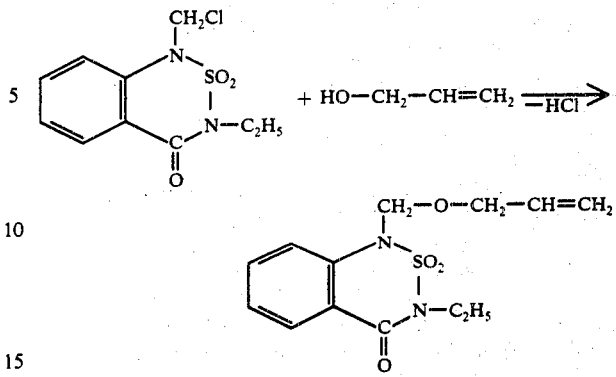

In a preferred embodiment of method a of the invention, a 3-alkyl-2,1,3-benzothiadiazin-(4)-one-2,2-dioxide is reacted continuously or batchwise with an α-halo ether in the presence or absence of an inert solvent and of an acid binder at a temperature of from −30° to +150° C, preferably +10° to +90° C, for from 10 minutes to 3 hours.

Examples of preferred inert solvents in method a of the invention are hydrocarbons such as ligroine, benzene, toluene, pentane, hexane, cyclohexane, and petroleum ether; halohydrocarbons such as methylene chloride, chloroform, carbon tetrachloride, 1,1- and 1,2-dichloroethane, 1,1,1- and 1,1,2-trichloroethane, chlorobenzene, o,m,p-dichlorobenzene, and o,m,p-chlorotoluene; nitrohydrocarbons such as nitrobenzene, nitroethane, and o,m,p-chloronitrobenzene; nitriles such as acetonitrile, butyronitrile, and isobutyronitrile; ethers such as diethyl ether, di-n-propyl ether, tetrahydrofuran, and dioxane; esters such as ethyl acetate, acetoacetic ester and isobutyl acetate; and amides such as formamide, methylformamide and dimethylformamide.

The acid binder may be any of those conventionally used. Preferred examples are alkali metal hydroxides, alkali metal carbonates and tertiary organic bases. The following compounds are particularly suitable: sodium hydroxide, sodium carbonate, sodium bicarbonate, triethylamine, pyridine, trimethylamine, α,β,γ-picoline, lutidine, N,N-dimethylaniline, N,N-dimethylcyclohexylamine, quinoline, tri-n-propylamine and tri-n-butylamine.

Starting materials I and II may be added in any order. Instead of an acid binder, the hydrogen halide which forms may also be expelled with an inert gas, for example nitrogen.

In addition to starting materials I, their alkali metal, alkaline earth metal and ammonium salts may advantageously be used as starting materials. The α-halo ethers used as starting materials II are advantageously employed in an amount of from 1 to 2, preferably from 1 to 1.2, moles per mole of starting material I.

In variation b of the process of the invention, for example a compound of the formula III is reacted continuously or batchwise with an alcohol of the formula IV, in the presence or absence of a solvent and of an acid binder at a temperature of from −20° to +150° C, preferably from +20° C to +100° C, for from 30 minutes to 3 hours.

The preferred inert solvents and binders described for method a may also be used in method b.

The following embodiment is particularly preferred. Starting material III is mixed with starting material IV, if desired in one of the abovementioned inert solvents, and the hydrogen halide which has formed is removed by heating to the abovementioned temperature range and/or by introducing an inert gas, for instance nitrogen. It may also be advantageous to employ as solvent an excess of alcohol of the formula IV, expediently in an amount of from 1 to 100 moles, especially from 2 to 50 moles, based on starting material III.

To isolate the compounds of the formula V from the reaction mixture in accordance with variations a and b of the invention, the reaction mixture is stirred — when water-miscible solvents are used — into a dilute aqueous alkali solution. The oil which separates out is if desired extracted, washed with water and dried. If only slightly polar solvents immiscible with water are employed, the reaction solution may also be extracted direct with dilute aqueous alkali solution and water. If desired, the reaction solution may be concentrated beforehand, taken up in a solvent immiscible with water, and purified as described above. The desired end products are obtained by drying and concentrating the organic phase. If desired, they may be further purified in conventional manner, e.g., by recrystallization or chromatography.

EXAMPLE 1

At 10° C and while stirring, 6.4 parts of chloromethyl methyl ether in 20 parts of methylene choride, and 8.3 parts of triethylamine in 15 parts of methylene chloride were introduced over a 7-minute period into a suspension of 18 parts of 3-ethyl-2,1,3-benzothiadiazin-(4)-one-2,2-dioxide in 500 parts of methylene chloride. The reaction mixture was stirred for 1 hour at 25° C, washed with water and extracted twice with 1N caustic soda solution (50 parts each time) and again with water. After drying over magnesium sulfate and concentration, there was obtained 20.3 parts (93% of theory) of 1-methoxymethyl-3-ethyl-2,1,3-benzothiadiazin-(4)-one-2,2-dioxide (I) as a colorless oil; $n_D^{25}$:1.5479.

EXAMPLE 2

At 10° C and while stirring, 33.5 parts of chloromethyl methyl ether in 40 parts of acetonitrile was introduced over a 40-minute period into a suspension of 109 parts of the sodium salt of 3-isopropyl-2,1,3-benzothiadiazin-(4)-one-2,2-dioxide in 1,200 parts of acetonitrile. The reaction mixture was stirred for 30 minutes at 25° C and then concentrated in vacuo. The residue was taken up in 500 parts of methylene chloride, washed with water and extracted twice with 0.5N caustic soda solution (each time with 150 parts) and again with water. After drying over magnesium sulfate and concentration, there was obtained 95 parts (80% of theory) of 1-methoxymethyl-3-isopropyl-2,1,3-benzothiadiazin-(4)-one-2,2-dioxide (II) as a colorless oil; $n_D^{25}$:1.5420.

EXAMPLE 3

At room temperature, 289 parts of 1-chloromethyl-3-isopropyl-2,1,3-benzothiadiazin-(4)-one-2,2-dioxide was introduced into 1,000 parts of absolute methanol. The reaction mixture was then stirred for 1 hour at 65° C and a slight stream of nitrogen was passed in. After concentration of the reaction solution in vacuo, the residue was taken up in 1,500 parts of methylene chloride and extracted three times with 100 ml of 1N caustic soda solution and with water. After drying over magnesium sulfate and concentration there was obtained 268 parts (94% of theory) of 1-methoxymethyl-3-isopropyl-2,1,3-benzothiadiazin-(4)-one-2,2-dioxide as a colorless oil; $n_D^{25}$:1.5420.

Further active ingredients of the formula V were prepared analogously. They are listed in Table 1, m denoting 0.

Table 1

| $R^1$ | $R^2$ | Y | n | m.p. |
|---|---|---|---|---|
| $CH_3$ | H | O | 2 | |
| H | $CH_3$ | O | 2 | |
| H | $C_2H_5$ | O | 2 | |
| H | $n\text{-}C_3H_7$ | O | 2 | |
| H | $i\text{-}C_3H_7$ | O | 2 | |
| H | $sec.C_4H_9$ | O | 2 | |
| $CH_3$ | $CH_3$ | O | 2 | 76–80° C |
| $CH_3$ | $C_2H_5$ | O | 2 | 68–72° C |
| $CH_3$ | $n\text{-}C_3H_7$ | O | 2 | $n_D^{25} = 1.5379$ |
| $CH_3$ | $i\text{-}C_3H_7$ | O | 2 | |
| $CH_3$ | ◁ | O | 2 | |
| $CH_3$ | $n\text{-}C_4H_9$ | O | 2 | |
| $CH_3$ | $CH_3$ | S | 2 | |
| $CH_3$ | $CH_3$ | O | 1 | |
| $CH_3$ | $i\text{-}C_3H_7$ | O | 1 | |
| $CH_3$ | $i\text{-}C_3H_7$ | S | 1 | |
| $CH_3$ | $i\text{-}C_4H_9$ | O | 2 | |
| $CH_3$ | $sec.C_4H_9$ | O | 2 | |
| $CH_3$ | $tert.C_4H_9$ | O | 2 | |
| $C_2H_5$ | H | O | 2 | |
| $C_2H_5$ | $C_2H_5$ | O | 2 | |
| $C_2H_5$ | $C_2H_5$ | O | 1 | |
| $C_2H_5$ | $n\text{-}C_3H_7$ | O | 2 | |
| $C_2H_5$ | $n\text{-}C_3H_7$ | S | 2 | |
| $C_2H_5$ | $i\text{-}C_3H_7$ | O | 2 | |
| $CH_3$ | $CH_2\text{—}C\equiv CH$ | O | 2 | 73–76° C |
| $C_2H_5$ | ◁ | O | 2 | |
| $C_2H_5$ | $n\text{-}C_4H_9$ | O | 2 | |
| $C_2H_5$ | $sec.C_4H_9$ | O | 2 | |
| $C_2H_5$ | $i\text{-}C_4H_9$ | O | 2 | |
| $C_2H_5$ | $tert.C_4H_9$ | O | 2 | |
| $C_2H_5$ | $i\text{-}C_3H_7$ | S | 2 | |
| $n\text{-}C_3H_7$ | H | O | 2 | |
| $n\text{-}C_3H_7$ | $CH_3$ | O | 2 | $n_D^{25} = 1.5428$ |
| $n\text{-}C_3H_7$ | $C_2H_5$ | O | 2 | |

Table 1-continued

| R¹ | R² | Y | n | m.p. |
|---|---|---|---|---|
| n-C₃H₇ | i-C₃H₇ | O | 2 | |
| n-C₃H₇ | i-C₃H₇ | O | 1 | |
| n-C₃H₇ | n-C₄H₉ | O | 2 | |
| n-C₃H₇ | i-C₄H₉ | O | 2 | |
| n-C₃H₇ | sec.C₄H₉ | O | 2 | |
| n-C₃H₇ | tert.C₄H₉ | O | 2 | |
| n-C₃H₇ | C₂H₅ | S | 2 | |
| n-C₃H₇ | cyclopropyl | O | 2 | |
| n-C₃H₇ | cyclohexyl-H | O | 2 | |
| n-C₃H₇ | C₁₀H₂₁ | O | 2 | |
| C₂H₅ | C₉H₁₉ | O | 2 | |
| n-C₃H₇ | n-C₅H₁₁ | O | 2 | |
| n-C₃H₇ | sec.C₄H₉ | O | 1 | |
| i-C₃H₇ | H | O | 2 | 95° C (decomposes) |
| i-C₃H₇ | C₂H₅ | O | 2 | $n_D^{25} = 1.5361$ |
| i-C₃H₇ | n-C₃H₇ | O | 2 | $n_D^{25} = 1.5270$ |
| i-C₃H₇ | i-C₃H₇ | O | 2 | 59–61° C |
| i-C₃H₇ | cyclopropyl | O | 2 | |
| i-C₃H₇ | CH₃ | S | 2 | 149° C |
| i-C₃H₇ | CH₃ | O | 1 | |
| i-C₃H₇ | n-C₄H₉ | O | 2 | $n_D^{25} = 1.5172$ |
| i-C₃H₇ | i-C₄H₉ | O | 2 | $n_D^{25} = 1.5178$ |
| i-C₃H₇ | sec.C₄H₉ | O | 2 | $n_D^{25} = 1.5109$ 53–55° C |
| i-C₃H₇ | sec.C₄H₉ | O | 1 | |
| i-C₃H₇ | C₂H₅ | S | 2 | |
| i-C₃H₇ | tert.C₄H₉ | O | 2 | 101–104° C |
| i-C₃H₇ | n-C₅H₁₁ | O | 2 | $n_D^{25} = 1.4972$ |
| i-C₃H₇ | —CH(n-C₃H₇)(CH₃) | O | 2 | |
| i-C₃H₇ | —CH(CH(CH₃)₂)(CH₃) | O | 2 | |
| i-C₃H₇ | —CH(C₂H₅)₂ | O | 2 | |
| i-C₃H₇ | —CH₂C(CH₃)₃ | O | 2 | |
| i-C₃H₇ | —CH₂—CH₂—CH(CH₃)₂ | O | 2 | |
| i-C₃H₇ | —C(CH₃)₂C₂H₅ | O | 2 | |
| i-C₃H₇ | —CH₂—CH(CH₃)—CH₂CH₃ | O | 2 | |
| i-C₃H₇ | cyclopentyl-H | O | 2 | |
| i-C₃H₇ | n-C₆H₁₃ | O | 2 | |
| i-C₃H₇ | cyclohexyl-H | O | 2 | $n_D^{25} = 1.5350$ |
| i-C₃H₇ | n-C₃H₇ | O | 1 | |
| i-C₃H₇ | n-C₅H₁₁ | O | 2 | |
| i-C₃H₇ | —CH(CH₃)—C(H)=CH₂ | O | 2 | $n_D^{25} = 1.5245$ 49–51° C |
| i-C₃H₇ | —CH(CH₃)—C≡CH | O | 2 | |
| i-C₃H₇ | CH₂—CH=CH—CH₃ | O | 2 | $n_D^{25} = 1.5170$ |
| i-C₃H₇ | CH₂—CH=CH₂ | O | 2 | $n_D^{25} = 1.5357$ |
| i-C₃H₇ | CH₂—C≡CH | O | 2 | 63–64° C |
| i-C₃H₇ | —CH(CH₃)—CH=CH₂ | S | 2 | |
| i-C₃H₇ | n-C₇H₁₅ | O | 2 | |
| i-C₃H₇ | n-C₈H₁₇ | O | 2 | |
| i-C₃H₇ | n-C₉H₁₉ | O | 2 | |
| i-C₃H₇ | n-C₁₀H₂₁ | O | 2 | $n_D^{25} = 1.4801$ |
| i-C₃H₇ | n-C₁₁H₂₃ | O | 2 | |
| i-C₃H₇ | n-C₁₂H₂₅ | O | 2 | $n_D^{25} = 1.4789$ |
| i-C₃H₇ | i-C₁₃H₂₇ | O | 2 | $n_D^{25} = 1.4850$ |
| i-C₃H₇ | n-C₁₄H₂₉ | O | 2 | |
| i-C₃H₇ | n-C₁₅H₃₁ | O | 2 | |
| i-C₃H₇ | n-C₁₆H₃₃ | O | 2 | |

Table 1-continued

| R¹ | R² | Y | n | m.p. |
|---|---|---|---|---|
| i-C₃H₇ | CH₃-CH-C(CH₃)=CH₂ | O | 2 | |
| i-C₃H₇ | CH₂CH₂F | O | 2 | $n_D^{25}$ = 1.5273 |
| i-C₃H₇ | CH₂CF₃ | O | 2 | 76-81° C |
| i-C₃H₇ | C(CH₃)₂CH=CH₂ | O | 2 | |
| i-C₃H₇ | C(CH₃)₂C≡CH | O | 2 | |
| i-C₃H₇ | C(CH₃)₂CH=CH₂ | O | 1 | |
| n-C₄H₉ | H | O | 2 | |
| n-C₄H₉ | CH₃ | O | 2 | |
| n-C₄H₉ | C₂H₅ | O | 2 | |
| n-C₄H₉ | CH(CH₃)₂ | O | 2 | |
| n-C₄H₉ | CH₃ | S | 2 | |
| n-C₄H₉ | CH₃ | O | 1 | |
| i-C₄H₉ | H | O | 2 | |
| i-C₄H₉ | CH₃ | O | 2 | $n_D^{25}$ = 1.5339 |
| i-C₄H₉ | C₂H₅ | O | 2 | |
| i-C₄H₉ | CH(CH₃)₂ | O | 2 | |
| sec.C₄H₉ | H | O | 2 | |
| sec.C₄H₉ | CH₃ | O | 2 | $n_D^{25}$ = 1.5381<br>45-48° C |
| sec.C₄H₉ | C₂H₅ | O | 2 | $n_D^{25}$ = 1.5319 |
| CH(C₂H₅)₂ | H | O | 2 | |
| CH(C₂H₅)₂ | CH₃ | O | 2 | 54-58° C |
| CH(C₂H₅)₂ | C₂H₅ | O | 2 | |
| CH(C₂H₅)₂ | CH(CH₃)₂ | O | 2 | |
| CH(C₂H₅)₂ | C(CH₃)₃ | O | 2 | |
| CH(C₂H₅)₂ | CH₃ | S | 2 | |
| CH(C₂H₅)₂ | CH₃ | O | 1 | |
| cyclopentyl | CH₃ | O | 2 | |
| cyclopentyl | C₂H₅ | O | 2 | |
| cyclopentyl | CH(CH₃)₂ | O | 2 | |
| cyclohexyl | H | O | 2 | |
| cyclohexyl | CH₃ | O | 2 | |
| cyclohexyl | C₂H₅ | O | 2 | |
| cyclohexyl | CH(CH₃)₂ | O | 2 | |
| CH(CH₃)(CH₂CH(CH₃)₂) | CH₃ | O | 2 | |
| CH(C₂H₅)((CH₂)₃CH₃) | CH₃ | O | 2 | |
| CH₂—CH₂—Cl | H | O | 2 | |
| CH₂—CH₂—Cl | CH₃ | O | 2 | 74-77° C |
| CH₂—CH₂—Cl | C₂H₅ | O | 2 | |
| CH₂—CH₂—Cl | CH(CH₃)₂ | O | 2 | |
| CH₂—CH₂—Cl | CH₃ | S | 2 | |
| CH₂—CH₂—Cl | CH₃ | O | 1 | |
| CH(CH₃)(CH₂Cl) | CH₃ | O | 2 | $n_D^{25}$ = 1.5511 |
| CH(CH₃)(CH₂Cl) | C₂H₅ | O | 2 | |
| CH(CH₃)(CH₂F) | CH₃ | O | 2 | |

Table 1-continued

| R¹ | R² | Y | n | m.p. |
|---|---|---|---|---|
| CH₃−CH(−CH₂F) | CH₃ | O | 1 | |
| CH₃ | CH₂−CH₂−Cl | O | 2 | |
| CH₃ | CH₂−CH₂−Cl | O | 1 | |
| CH₃ | CH₃−CH(−CH₂F) | O | 2 | |
| C₂H₅ | CH₂−CH₂−Cl | O | 2 | |
| C₂H₅ | CH₂−CH₂Br | O | 2 | |
| C₂H₅ | CH(CF₃)₂ | O | 2 | |
| n-C₃H₇ | CH₂−CH₂−Cl | O | 2 | |
| n-C₃H₇ | CH₂−C≡C−CH₂−Cl | O | 2 | |
| i-C₃H₇ | CH₂−CH₂−Cl | O | 2 | $n_D^{25} = 1.5241$ |
| i-C₃H₇ | CH₃−CH(−CH₂F) | O | 2 | |
| i-C₃H₇ | CH₂−CH(Cl)−CH=CH₂ | O | 2 | |
| i-C₃H₇ | CH₂−CH=CH−CH₂Cl | O | 2 | |
| n-C₄H₉ | CH₂−CH₂Cl | O | 2 | |
| n-C₄H₉ | CH₃−CH(−CH₂Cl) | O | 2 | |
| i-C₄H₉ | CH₂−CH₂Cl | O | 2 | |
| i-C₄H₉ | C(CH₃)₂C≡CH | O | 2 | |
| sec.C₄H₉ | CH₂−CH₂Cl | O | 2 | |
| sec.C₄H₉ | CH₂−CH₂−Cl | O | 1 | |
| sec.C₄H₉ | CH₂−CH=CH₂ | O | 2 | |
| sec.C₄H₉ | CH₃−CH(−CH₂F) | O | 2 | |
| sec.C₄H₉ | CH₂−CH=CH−CH₂Cl | O | 2 | |
| sec.C₄H₉ | C(CH₃)₂C≡CH | O | 2 | |
| sec.C₄H₉ | C(CH₃)₂CH=CH₂ | O | 2 | |
| sec.C₄H₉ | CH₂−C(Cl)−CH=CH₂ | O | 2 | |
| sec.C₄H₉ | CH₂−C≡C−CH₂Cl | O | 2 | |
| CH(C₂H₅)₂ | CH₂−CH=CH₂ | O | 1 | |
| CH(C₂H₅)₂ | CH₂−CH₂−Cl | O | 2 | |
| CH(C₂H₅)₂ | CH₃−CH(−CH₂F) | S | 2 | |
| H | CH₂CH₂−O−CH₃ | O | 2 | |
| CH₃ | CH₂CH₂−O−CH₃ | O | 2 | |
| C₂H₅ | CH₂CH₂−O−CH₃ | O | 2 | |
| C₂H₅ | CH₂CH₂−O−CH₃ | O | 1 | |
| C₂H₅ | CH₂CH₂CH₂−O−CH₃ | O | 2 | |
| i-C₃H₇ | CH₂CH₂−O−CH₃ | O | 2 | $n_D^{25} = 1.5305$ |
| i-C₃H₇ | CH₂CH₂−O−n-C₄H₉ | O | 2 | $n_D^{25} = 1.5156$ |
| n-C₃H₇ | C₂H₅−CH(−CH₂−OCH₃) | O | 2 | |
| n-C₃H₇ | CH₃−CH(−CH₂OCH₃) | S | 2 | |
| n-C₃H₇ | CH₃−CH(−CH₂OCH₃) | O | 2 | |
| i-C₃H₇ | CH₃−CH(−CH₂OCH₃) | O | 2 | $n_D^{25} = 1.5204$ |
| i-C₃H₇ | C(CH₃)₂−CH₂−OCH₃ | O | 2 | |
| sec.C₄H₉ | CH₂−CH₂−OCH₃ | O | 2 | |

Table 1-continued

| R¹ | R² | Y | n | m.p. |
|---|---|---|---|---|
| sec.C₄H₉ | CH₃-CH-CH₂O-CH₃ | O | 2 | |
| n-C₄H₉ | CH₂—CH₂—OCH₃ | O | 2 | |
| H | CH₂—CH₂—S—CH₃ | O | 2 | |
| CH₃ | CH₂—CH₂—S—CH₃ | O | 2 | |
| CH₃ | CH₂—CH(CH₃)—S—CH₃ | O | 2 | |
| CH₃ | CH₂—CH(CH₃)—S—CH₃ | O | 1 | |
| C₂H₅ | CH₂—CH₂—S—CH₃ | S | 2 | |
| C₂H₅ | CH₂—CH₂—S—C₂H₅ | O | 2 | |
| C₂H₅ | CH(C₂H₅)—CH₂—S—CH₃ | O | 2 | |
| n-C₃H₇ | CH₂—CH₂—S—CH₃ | O | 2 | |
| n-C₃H₇ | CH(CH₃)—CH₂—S—CH₃ | O | 2 | |
| i-C₃H₇ | CH₂—CH₂—S—CH(CH₃)₂ | O | 2 | $n_D^{25} = 1.5390$ |
| i-C₃H₇ | CH₂—CH₂—S—CH₃ | S | 2 | |
| i-C₃H₇ | CH₂—CH₂—S—CH₃ | O | 2 | |
| i-C₃H₇ | CH(CH₃)—CH₂—S—CH₃ | O | 2 | |
| sec.C₄H₉ | CH₂—CH₂—S—CH₃ | O | 2 | |
| sec.C₄H₉ | CH(CH₃)—CH₂—S—CH₃ | O | 2 | |
| H | C(CH₃)₂—C(=O)—CH₃ | O | 2 | |
| CH₃ | C(CH₃)₂—C(=O)—CH₃ | O | 2 | |
| C₂H₅ | CH(CH₃)—C(=O)—CH₃ | O | 2 | |
| n-C₃H₇ | CH(CH₃)—C(=O)—CH₃ | O | 2 | |
| n-C₃H₇ | CH₂—CH₂—C(=O)—CH₃ | O | 2 | |
| i-C₃H₇ | CH₂—CH₂—C(=O)—CH₃ | O | 2 | $n_D^{25} = 1.5370$ |
| i-C₃H₇ | CH(CH₃)—C(=O)—CH₃ | O | 2 | |
| i-C₃H₇ | C(CH₃)₂—C(=O)—CH₃ | O | 2 | |
| i-C₃H₇ | C(CH₃)₂—C(=O)—CH₃ | S | 2 | |
| n-C₄H₉ | CH₂—CH₂—C(=O)—CH₃ | O | 1 | |
| n-C₄H₉ | CH₂—CH₂—C(=O)—CH₃ | O | 2 | |

Table 1-continued

| R¹ | R² | Y | n | m.p. |
|---|---|---|---|---|
| n-C₄H₉ | $\text{CH}_3-\underset{\underset{O}{\|}}{\overset{\|}{\text{CH}}}-\text{CH}_3$ (CH with C(=O)CH₃) | O | 2 | |
| H | CH₂—CO₂CH₃ | O | 2 | |
| CH₃ | CH₂—CO₂CH₃ | O | 2 | |
| C₂H₅ | CH₂—CO₂CH₃ | O | 2 | |
| C₂H₅ | CH₂CH₂CO₂CH₃ | O | 2 | |
| C₂H₅ | CH(CH₃)CO₂C₂H₅ | O | 2 | |
| C₂H₅ | CH₂—CH₂CO₂CH₃ | O | 1 | |
| C₂H₅ | CH₂—CH₂CO₂CH₃ | S | 2 | |
| n-C₃H₇ | CH₂CO₂CH₃ | O | 2 | |
| i-C₃H₇ | CH₂CO₂CH₃ | O | 2 | |
| i-C₃H₇ | CH(CH₃)CO₂C₂H₅ | O | 2 | |
| i-C₃H₇ | CH₂CH₂CO₂CH₃ | O | 2 | |
| sec.C₄H₉ | CH₂CO₂CH₃ | O | 2 | |
| sec.C₄H₉ | CH(CH₃)CO₂CH₃ | O | 2 | |
| n-C₄H₉ | CH₂CO₂CH₃ | O | 2 | |
| CH₃ | C(CH₃)(CH=CH₂)CO₂CH₃ | O | 2 | |
| C₂H₅ | C(CH₃)(CH=CH₂)CO₂CH₃ | O | 2 | |
| i-C₃H₇ | C(CH₃)(CH=CH₂)CO₂CH₃ | O | 2 | |
| n-C₃H₇ | C(H)(CH=CH₂)CO₂CH₃ | O | 2 | |
| sec.C₄H₉ | C(H)(CH=CH₂)CO₂CH₃ | O | 2 | |
| CH₃ | C(CH₃)₂CH₂Cl | O | 2 | |
| C₂H₅ | C(CH₃)₂CH₂Cl | O | 2 | |
| n-C₃H₇ | C(CH₃)₂CH₂Cl | O | 2 | |
| i-C₃H₇ | C(CH₃)₂CH₂Cl | O | 2 | |
| n-C₄H₉ | C(CH₃)₂CH₂Cl | O | 2 | |
| i-C₃H₇ | C(H)(CH=CH₂)CO₂CH₃ | O | 2 | $n_D^{25} = 1.5349$ |
| sec.C₃H₉ | C(CH₃)₂CH₂Cl | O | 1 | |
| sec.C₄H₉ | C(CH₃)₂CH₂Cl | O | 2 | |
| ⟨H⟩ (phenyl) | C(CH₃)₂CH₂Cl | O | 2 | |
| i-C₃H₇ | C(CH₃)₂O₂H₅ | O | 2 | |
| sec.C₄H₉ | C(CH₃)₂C₂H₅ | O | 2 | |
| sec.C₄H₉ | CH(CH₃)₂ | O | 2 | |
| i-C₃H₇ | CH₂—C(=O)—NHCH₃ | O | 2 | |
| C₂H₅ | CH₂—C(=O)—N(CH₃)₂ | O | 2 | |
| i-C₃H₇ | CH₂—C(=O)—N(C₂H₅)₂ | O | 2 | |
| i-C₃H₇ | —CH₂—C(=O)—N(CH₃)₂ | O | 2 | |

Table 1-continued

| R¹ | R² | Y | n | m.p. |
|---|---|---|---|---|
| i-C₃H₇ | —CH₂—(cyclohexyl) | | | |

Table 2

| X | Ring position | m | R¹ | R² | Y | n | m.p. |
|---|---|---|---|---|---|---|---|
| CH₃ | 5,6,7,8 | 1 | CH₃ | CH₃ | O | 2 | |
| CH₃ | 5,6,7,8 | 1 | C₂H₅ | CH₃ | O | 2 | |
| CH₃ | 5,6,7,8 | 1 | n-C₃H₇ | CH₃ | O | 2 | |
| CH₃ | 8 | 1 | i-C₃H₇ | CH₃ | O | 2 | 109–111° C |
| CH₃ | 8 | 1 | i-C₃H₇ | C₂H₅ | O | 2 | |
| CH₃ | 8 | 1 | i-C₃H₇ | C(CH₃)₃ | O | 2 | |
| CH₃ | 8 | 1 | i-C₃H₇ | CH₃ | S | 2 | |
| CH₃ | 8 | 1 | i-C₃H₇ | CH₃ | O | 1 | |
| CH₃ | 8 | 1 | i-C₃H₇ | C₂H₅ | O | 1 | |
| CH₃ | 8 | 1 | i-C₃H₇ | CH(CH₃)₂ | O | 2 | |
| CH₃ | 8 | 1 | i-C₃H₇ | CH₂—CH=CH₂ | O | 2 | |
| CH₃ | 8 | 1 | sec.C₄H₉ | CH₃ | O | 2 | |
| CH₃ | 8 | 1 | sec.C₄H₉ | CH₃ | O | 1 | |
| CH₃ | 6,8 | 2 | i-C₃H₇ | CH₃ | O | 2 | |
| Br | 6 | 1 | i-C₃H₇ | CH₃ | O | 2 | $n_D^{25} = 1.5641$ |
| Br | 5,6,7,8 | 1 | i-C₃H₇ | C₂H₅ | O | 2 | |
| Br | 5,7,8 | 1 | i-C₃H₇ | CH₃ | O | 2 | |
| Br | 6,8 | 2 | i-C₃H₇ | CH₃ | O | 2 | 93–98° C |
| Br | 6 | 1 | sec.C₄H₉ | CH₃ | O | 2 | |
| Cl | 5,6,7,8 | 1 | i-C₃H₇ | CH₃ | O | 2 | |
| Cl | 5,6,7,8 | 1 | n-C₃H₇ | CH₃ | O | 2 | |
| Cl | 6,8 | 2 | i-C₃H₇ | CH₃ | O | 2 | |
| Cl | 6,8 | 2 | i-C₃H₇ | CH₃ | O | 1 | |
| F | 5,6,7,8 | 1 | i-C₃H₇ | CH₃ | O | 2 | |
| Cl | 7 | 1 | i-C₃H₇ | CH₃ | O | 2 | 59–64° C |
| Cl | 8 | 1 | i-C₃H₇ | CH₃ | O | 2 | 66–70° C |
| F | 5,6,7,8 | 4 | i-C₃H₇ | CH₃ | O | 2 | |
| {CH₃, Cl} | {6, 8} | 2 | i-C₃H₇ | CH₃ | O | 2 | |
| {CH₃, Cl} | {8, 6} | 2 | i-C₃H₇ | CH₃ | O | 2 | |
| cyclopropyl | 8 | 1 | i-C₃H₇ | CH₃ | O | 2 | |
| C₆H₅ | 5,6,7,8 | 1 | i-C₃H₇ | CH₃ | O | 2 | |
| C₆H₅ | 5,6,7,8 | 1 | sec.C₄H₉ | CH₃ | O | 2 | |
| C₆H₅ | 5,6,7,8 | 1 | n-C₃H₇ | CH₃ | O | 2 | |
| Cl—C₆H₄— | 5,6,7,8 | 1 | i-C₃H₇ | CH₃ | O | 2 | |
| Cl—C₆H₄— | 5,6,7,8 | 1 | i-C₃H₇ | CH₃ | O | 2 | |
| F—C₆H₄— | 5,6,7,8 | 1 | i-C₃H₇ | CH₃ | O | 2 | |
| F—C₆H₄— (meta) | 5,6,7,8 | 1 | i-C₃H₇ | C₂H₅ | O | 2 | |
| Cl—C₆H₃(F)—CH₂ | 5,6,7,8 | 1 | i-C₃H₇ | CH₃ | O | 2 | |
| | 5,6,7,8 | 1 | n-C₃H₇ | CH₃ | O | 2 | |
| CH₃—C₆H₄— | 5,6,7,8 | 1 | i-C₃H₇ | CH₃ | O | 2 | |
| CH₃—C₆H₄— (meta) | 5,6,7,8 | 1 | i-C₃H₇ | CH₃ | O | 2 | |
| NO₂ | 5,6,7,8 | 1 | i-C₃H₇ | CH₃ | O | 1 | |
| N(CH₃)₂ | 5,6,7,8 | 1 | i-C₃H₇ | CH₃ | O | 1 | |
| OCH₃ | 5,6,7,8 | 1 | i-C₃H₇ | CH₃ | O | 2 | |
| OCH₃ | 5,6,7,8 | 1 | sec.C₄H₉ | C₂H₅ | O | 2 | |
| OCH₃ | 5,6,7,8 | 1 | i-C₃H₇ | CH₂—CH=CH₂ | O | 2 | |
| SCH₃ | 5,6,7,8 | 1 | C₂H₅ | CH₃ | O | 1 | |
| SCH₃ | 5,6,7,8 | 1 | i-C₃H₇ | CH₃ | O | 2 | |
| SO₂CH₃ | 5,6,7,8 | 1 | CH₃ | CH₃ | O | 2 | |
| SO₂CH₃ | 5,6,7,8 | 1 | i-C₃H₇ | CH₃ | O | 2 | |
| SO₂CH₃ | 5,6,7,8 | 1 | sec.C₄H₉ | CH₃ | O | 2 | |
| SO₂OCH₃ | 5,6,7,8 | 1 | i-C₃H₇ | C₂H₅ | O | 2 | |

Table 2-continued

| X | Ring position | m | R¹ | R² | Y | n | m.p. |
|---|---|---|---|---|---|---|---|
| SO₂OCH₃ | 5,6,7,8 | 1 | i-C₃H₇ | i-C₃H₇ | O | 2 | |
| SO₂N(CH₃)₂ | 5,6,7,8 | 1 | i-C₃H₇ | CH₃ | S | 2 | |
| SO₂N(CH₃)₂ | 5,6,7,8 | 1 | i-C₃H₇ | CH₃ | O | 2 | |
| CCl₃ | 5,6,7,8 | 1 | i-C₃H₇ | CH₃ | O | 2 | |
| CCl₃ | 5,6,7,8 | 1 | C₂H₅ | CH₂—CH=CH₂ | O | 2 | |
| CF₃ | 5,6,7,8 | 1 | i-C₃H₇ | CH₃ | O | 2 | |
| CF₃ | 5,6,7,8 | 1 | i-C₃H₇ | C₂H₅ | O | 2 | |
| CF₃ | 5,6,7,8 | 1 | i-C₃H₇ | i-C₃H₇ | O | 2 | |
| $\overset{O}{\underset{\parallel}{C}}-CH_3$ | 5,6,7,8 | 1 | i-C₃H₇ | CH₃ | O | 2 | |
| $\overset{O}{\underset{\parallel}{C}}-H$ | 5,6,7,8 | 1 | i-C₃H₇ | CH₃ | O | 2 | |
| OH | 5,6,7,8 | 1 | i-C₃H₇ | CH₃ | O | 2 | |
| SH | 5,6,7,8 | 1 | i-C₃H₇ | CH₃ | O | 2 | |
| SO₂NHCH₃ | 5,6,7,8 | 1 | i-C₃H₇ | CH₃ | O | 2 | |
| SO₂NHC₂H₅ | 5,6,7,8 | 1 | C₂H₅ | CH₂—CH=CH₂ | O | 2 | |
| Cl | 5,6,7,8 | 1 | 3-F-C₆H₄ | CH₃ | O | 2 | |
| CH₃ | 5,6,7,8 | 1 | C₆H₅ | CH₃ | O | 2 | |
| CH₃ | 5,6,7,8 | 1 | 3-F-C₆H₄ | CH₃ | O | 2 | |
| | | 0 | cyclopropyl | CH₃ | O | 2 | |
| | | 0 | cyclopropyl | C₂H₅ | O | 2 | |
| | | 0 | cyclopropyl | CH₂—CH=CH₂ | O | 2 | |
| | | 0 | cyclopropyl | i-C₃H₇ | O | 2 | |
| | | 0 | C(CH₃)₃ | CH₃ | O | 2 | |
| | | 0 | C(CH₃)₃ | C₂H₅ | O | 2 | |
| CH₃ | 5,6,7,8 | 1 | cyclopropyl | CH₃ | O | 2 | |
| Cl | 5,6,7,8 | 1 | cyclopropyl | CH₃ | O | 2 | |
| | | 0 | CH₂CH=CH₂ | CH₃ | O | 2 | |
| | | 0 | CH₂CH=CH₂ | C₂H₅ | O | 2 | |
| | | 0 | CH₂CH=CH₂ | i-C₃H₇ | O | 2 | |
| CH₃ | 5,6,7,8 | 1 | CH₂CH=CH₂ | CH₃ | O | 2 | |
| CH₃ | 5,6,7,8 | 1 | C(CH₃)₃ | CH₃ | O | 2 | |
| Cl | 5,6,7,8 | 1 | CH₂CH=CH₂ | CH₃ | O | 2 | |
| | | 0 | CH(CH₃)CH=CH₂ | CH₃ | O | 2 | |
| | | 0 | CH(CH₃)CH=CH₂ | CH₃ | S | 2 | |
| CH₃ | 5,6,7,8 | 1 | CH(CH₃)CH=CH₂ | CH₃ | O | 2 | |
| Cl | 5,6,7,8 | 1 | CH(CH₃)CH=CH₂ | CH₃ | O | 2 | |
| | | 0 | CH(CH₃)CH=CH₂ | CH₃ | O | 2 | |
| | | 0 | CH(CH₃)C≡CH | C₂H₅ | O | 2 | |

Table 2-continued

| X | Ring position | m | R¹ | R² | Y | n | m.p. |
|---|---|---|---|---|---|---|---|
|  |  | 0 | CH(CH₃)-C≡CH | i-C₃H₇ | O | 2 |  |
| CH₃ | 5,6,7,8 | 1 | CH(CH₃)-C≡CH | CH₃ | O | 2 |  |
| Cl | 5,6,7,8 | 1 | CH(CH₃)-C≡CH | CH₃ | O | 2 |  |
|  |  | 0 | CH₂-C(CH₃)=CH₂ | CH₃ | O | 2 |  |
| CH₃ | 5,6,7,8 | 1 | CH₂-C(CH₃)=CH₂ | CH₃ | O | 2 |  |
|  |  | 0 | CH(CH₃)-CH₂-OCH₃ | CH₃ | O | 2 |  |
| CH₃ | 5,6,7,8 | 1 | CH(CH₃)-CH₂-OCH₃ | CH₃ | O | 2 |  |

EXAMPLE 4

90 parts by weight of compound I is mixed with 10 parts by weight of N-methyl-α-pyrrolidone. A mixture is obtained which is suitable for application in the form of very fine drops.

EXAMPLE 5

20 parts by weight of compound II is dissolved in a mixture consisting of 80 parts by weight of xylene, 10 parts by weight of the adduct of 8 to 10 moles of ethylene oxide to 1 mole of oleic acid-N-monoethanolamide, 5 parts by weight of the calcium salt of dodecylbenzenesulfonic acid, and 5 parts by weight of the adduct of 40 moles of ethylene oxide to 1 mole of castor oil. By pouring the solution into 100,000 parts by weight of water and uniformly distributing it therein, an aqueous dispersion is obtained containing 0.02% by weight of the active ingredient.

EXAMPLE 6

20 parts by weight of compound I is dissolved in a mixture consisting of 40 parts by weight of cyclohexanone. 30 parts by weight of isobutanol, 20 parts by weight of the adduct of 7 moles of ethylene oxide to 1 mole of isooctylphenol, and 10 parts by weight of the adduct of 40 moles of ethylene oxide to 1 mole of castor oil. By pouring the solution into 100,000 parts by weight of water and uniformly distributing it therein, an aqueous dispersion is obtained containing 0.02% by weight of the active ingredient.

EXAMPLE 7

20 parts by weight of compound I is dissolved in a mixture consisting of 25 parts by weight of cyclohexanol, 65 parts by weight of a mineral oil fraction having a boiling point between 210° and 280° C, and 10 parts by weight of the adduct of 40 moles of ethylene oxide to 1 mole of castor oil. By pouring the solution into 100,000 parts by weight of water and uniformly distributing it therein, an aqueous dispersion is obtained containing 0.02% by weight of the active ingredient.

EXAMPLE 8

20 parts by weight of compound II is well mixed with 3 parts by weight of the sodium salt of diisobutylnaphthalene-α-sulfonic acid, 17 parts by weight of the sodium salt of a lignin-sulfonic acid obtained from a sulfite waste liquor, and 60 parts by weight of powdered silica gel, and triturated in a hammer mill. By uniformly distributing the mixture in 20,000 parts by weight of water, a spray liquid is obtained containing 0.1% by weight of the active ingredient.

EXAMPLE 9

3 parts by weight of compound I is intimately mixed with 97 parts by weight of particulate kaolin. A dust is obtained containing 3% by weight of the active ingredient.

EXAMPLE 10

30 parts by weight of compound I is intimately mixed with a mixture consisting of 92 parts by weight of powdered silica gel and 8 parts by weight of paraffin oil which has been sprayed onto the surface of this silica gel. A formulation of the active ingredient is obtained having good adherence.

EXAMPLE 11

40 parts by weight of compound I is intimately mixed with 10 parts of the sodium salt of a phenolsulfonic acid/urea/formaldehyde condensate, 2 parts of silica gel, and 48 parts of water. A stable aqueous dispersion is obtained. By dilution with 100,000 parts by weight of water an aqueous dispersion is obtained containing 0.04 wt% of active ingredient.

EXAMPLE 12

20 parts of compound II is intimately mixed with 2 parts of the calcium salt of dodecylbenzenesulfonic acid, 8 parts of a fatty alcohol polyglycol ether, 2 parts of the sodium salt of a phenolsulfonic acid/urea/formaldehyde condensate, and 68 parts of a paraffinic mineral oil. A stable oily dispersion is obtained.

EXAMPLE 13

I. Material and methods

1. The following results were obtained under greenhouse conditions. The vessels were paraffined paper cups having a volume of 200 cm³, and which were filled with a sandy loam. The test plants were sown separately according to species. The following species were examined.

| Scientific term | Abbreviation in tables |
|---|---|
| Abutilon theophrastii | Abut. theoph. |
| Amaranthus retroflexus | Amar. retr. |
| Ammannia coccinea | Ammann. cocc. |
| Avena sativa | Avena sativa |
| Beta vulgaris altissima | Beta vulg. |
| Chenopodium album | Chenop. album |
| Cyperus difformis | Cyper. diff. |
| Cyperus esculentus | Cyper. escul. |
| Cyperus rotundus | Cyperus rotundus |
| Daucus carota | Daucus carota |
| Glycine max | Glyc. max. |
| Gossypium hirsutum | Gossyp. hirs. |
| Helianthus annuus | Helianth. annuus |
| Hordeum vulgare | Hord. vulg. |
| Ipomoea spp. | Ipom. spp. |
| Lolium multiflorum | Lolium multifl. |
| Ludwigia prostrata | Ludw. pros. |
| Mentha piperita | Mentha piper. |
| Monochoria vaginalis | Monoch. vagin. |
| Oryza sativa | Oryza sat. |
| Portulaca oleracea | Port. olerac. |
| Sesbania exaltata | Sesban. exalt. |
| Sida spinosa | Sida spin. |
| Sinapis alba | Sinapis alba |
| Stellaria media | Stell. med. |
| Triticum aestivum | Tritic. aestiv. |
| Xanthium pennsylvanicum | Xant. pennsyl. |
| Zea mays | Zea mays |

Generally, the compounds investigated were suspended or emulsified in 500 to 1,000 liters/ha of water. In some cases the soil was treated before germination of the seeds (Table 7); mostly, however, the young plants were treated. The growth height of the plants varied from 3 to 20 cm, depending on species and development. The experiments were carried out in accordance with the temperature needs of the plants employed; some in a warm range (20° - 30° C), others in a cooler range (16° - 23° C). It is known that the action of Bentazon — even in the case of very sensitive species — is influenced to a considerable extent by the development stage of the plants and the ecological conditions before and after treatment (Behrendt and Menck, 1973 +). This knowledge simplifies the interpretation of average values of experiments giving excellent and less good results.
+ Behrendt, S. and B. H. Menck, lecture held at 39th German Crop Protection Conference, Stuttgart, Oct. 1-5, 1973

2. The prior art compounds used for comparison purposes were 3-isopropyl-2,1,3-benzothiadiazin-(4)-one-2,2-dioxide (German 1,542,836 — Bentazon), 8-methyl-3-isopropyl-2,1,3-benzothiadiazin-(4)-one-2,2-dioxide (German Laid-Open Application DOS 2,443,901), 6,8-dichloro-3-isopropyl-2,1,3-benzothiadiazin-(4)-one-2,2-dioxide (German Laid-Open Application DOS 2,444,383), 1(α-ethoxy)-ethyl-3-isopropyl-2,1,3-benzothiadiazin-(4)-one-2,2-dioxide and 1-(α-methoxy)-ethyl-3-isopropyl-2,1,3-benzothiadiazin-(4)-one-2,2-dioxide (German Laid-Open Application DOS 2,355,113).

In some cases a prior art non-phytotoxic oil (emulsifiable vegetable oil) was added as wetting agent. The particular value of this type of oil for Bentazon is reported in the literature (Nalewaja, 1974 ++).
++ Nalewaja, J. Weeds Today, Fall, 1974

The application rates for the active ingredients varied from 0.125 to 4 kg/ha.

The experiments were evaluated after from 2 to 4 weeks. The values in the tables are averages of from 1 to 19 individual values of groupable experiments, 0 denoting no damage and 100 total destruction, based on untreated control plants.

II. Results

The best compound is 1-methoxymethyl-3-isopropyl-2,1,3-benzothiadiazin-(4)-one-2,2-dioxide. It surprisingly stands out from the comparative compounds in the following points:

1. Certain weed species are better controlled, which is an addition to the spectrum of activity previously known (e.g. Amaranthus retroflexus, Cyperus esculentus, Ipomoea spp., Portulaca oleracea, Tables 3, 4, 5 and 6). This advantage is particularly apparent in weed species important in cotton-growing areas.

2. The excellent and safe tolerance by cotton of this compound clearly exceeds that of prior art compounds for this crop (Table 3). The addition of oils as wetting agents to improve the herbicidal action of chemicals is common practice. It is often the case that the improvement in weed control is accompanied by damage to crops. However, no damage to cotton occurred with 1-methoxymethyl-3-isopropyl-2,1,3-benzothiadiazin-(4)-one-2,2-dioxide when oil was added to the spray liquor. This underlines the insensitivity of this crop to the active ingredient (Table 6).

3. The compound offers for the first time the opportunity of using such substances for removing unwanted plants from crops of the Umbelliferae family, such as carrots (Daucus carota), and Compositae family, such as sunflowers (Helianthus annuus). This is surprising, as prior art compounds of a similar structure totally destroy plants belonging to precisely these families (e.g. Matricaria spp.) (Table 5).

4. In crops of the Leguminosae (e.g. soybeans), Gramineae (e.g. rice, cereals, Indian corn), Labiatae (e.g. peppermint) (Tables 3, 4 and 5), Solanaceae (e.g. potatoes), Liliaceae (e.g. onions), Linaceae (e.g. flax) and Cucurbitaceae (e.g. cucumbers) families the new compound may be used just as prior art compounds.

5. The compounds provides good control of weed species on which the prior art compound 8-methyl-3-isopropyl-2,1,3-benzothiadiazin-(4)-one-2,2-dioxide has only a weak action, and vice versa. Admixture of this prior art compound, which is tolerated at least to a certain extent by cotton, to the new fully tolerated compound gives a herbicide having an excellent action and application spectrum (Table 8).

6. Not only this compound but also other compounds of the invention have an excellent herbicidal action (Tables 3, 4 and 5).

7. The ability of the new compound to damage or kill sensitive species when applied before germination or emergence of the test plants is demonstrated (Table 7).

8. Higher application rates than those given in the tables intensify the action on unwanted plants and also take in those considered to be difficult to control for compounds of this structure.

Table 3

Control of a typical weed flora in cotton (*Gossypium hirsutum*) and soybeans (*Glycine max*) - postemergence treatment Basic molecule of active ingredient $$\text{benzothiadiazinone ring system with positions 1, 2(SO}_2\text{), 3(N), 4(=O), 5, 6, 7, 8}$$

| Substituted in position | | | Application rate | % damage to test plants[+] | | | | | | | |
|---|---|---|---|---|---|---|---|---|---|---|---|
| 1 | 3 | 8 | kg/ha | Gossyp. hirs. | Glyc. max | Abut. theoph. | Cyper. escul. | Ipom. spp. | Sesban. exalt. | Sida spin. | Xanth. pennsyl. |
| CH$_3$—CH—O—C$_2$H$_5$ | C$_3$H$_7$i | H | 0.5 | 92 | 0 | 82 | 14 | 15 | 15 | 67 | — |
|  |  |  | 2.0 | 92.5 | 4 | 97 | 47 | 30 | 48 | 98 | 40 |
| prior art |  |  | 4.0 | 92.5 | 10 | — | 40 | 40 | 73 | 98 | 65 |
| CH$_3$—CH—O—CH$_3$ | C$_3$H$_7$i | H | 0.5 | 50 | 0 | 82 | 29 | 15 | 21 | 80 | — |
|  |  |  | 2.0 | 70 | 3 | 97 | 48 | 22 | 46 | 95 | 52 |
| prior art |  |  | 4.0 | 92 | 15 | — | 50 | 30 | — | 98 | 60 |
| H | C$_3$H$_7$i | H | 0.5 | 56 | 0 | 64 | 26 | 22 | 30 | 79 | 51 |
|  |  |  | 2.0 | 76 | 4 | 95 | 46 | 44 | 48 | 95 | 57 |
| prior art |  |  | 4.0 | 83 | 7 | — | 53 | 54 | 52 | 97 | 70 |
| H | C$_3$H$_7$i | CH$_3$ | 0.5 | 12 | 0 | 60 | 4 | 16 | 62 | 22 | 65 |
|  |  |  | 2.0 | 25 | 5 | 90 | 7 | 33 | 87 | 66 | 62 |
| prior art |  |  | 4.0 | 48 | 10 | — | 25 | 45 | 92 | 77 | — |
| H | C$_3$H$_7$i | Cl(6)[+++] | 0.5 | 20 | 10 | — | 10 | — | — | — | — |
| prior art |  | Cl | 1.0 | 80 | 20 | — | 10 | — | — | — | — |
|  |  |  | 2.0 | 80 | 20 | — | 50 | — | — | — | — |
| CH$_2$—O—CH$_3$ | C$_3$H$_7$i | H | 0.5 | 1 | 0 | 46 | 30 | 27 | 26 | 74 | 51 |
|  |  |  | 2.0 | 7 | 4 | 84 | 76 | 65 | 66 | 96 | 56 |
|  |  |  | 4.0 | 16 | 7 | — | 86 | 68 | 73 | 97 | 70 |
| CH$_2$—O—C$_2$H$_5$ | C$_3$H$_7$i | H | 0.5 | 0 | 5 | 30 | 27 | 22 | 15 | 87 | 50 |
|  |  |  | 2.0 | 20 | 15 | — | 74 | 52 | 82 | 97 | — |
|  |  |  | 4.0 | 32 | 20 | — | — | — | — | — | — |
| CH$_2$—O—C$_3$H$_7$i | C$_3$H$_7$i | H | 0.5 | — | 0 | 30 | 57 | 30 | 80 | 55 | — |
|  |  |  | 2.0 | 80 | 10 | — | 85 | 55 | 80 | 97 | 100 |
|  |  |  | 4.0 | 95 | 10 | — | — | — | — | — | — |
| CH$_2$—O—C$_3$H$_7$n | C$_3$H$_7$i | H | 0.5 | — | 0 | 90 | 30 | 37 | 50 | 65 | — |
|  |  |  | 2.0 | 60 | 10 | — | 67 | 55 | 80 | 97 | 100 |
|  |  |  | 4.0 | 60 | 20 | — | — | — | — | — | — |
| CH$_2$—O—CH$_3$ | C$_3$H$_7$n |  | 0.5 | — | 0 | 5 | 0 | 0 | — | 5 | 0 |
|  |  |  | 2.0 | 0 | 10 | — | 10 | 10 | 20 | 7 | — |
|  |  |  | 4.0 | 0 | 10 | — | 30 | — | — | — | — |
| CH$_2$—O—CH$_3$ | C$_2$H$_5$ | H | 0.5 | — | 0 | 5 | 30 | 0 | — | 5 | 10 |
|  |  |  | 2.0 | 0 | 5 | — | 55 | 13 | 30 | — | — |
|  |  |  | 4.0 | 10 | 10 | — | 60 | — | — | — | — |
| CH$_2$—O—CH$_3$ | —CH(C$_2$H$_5$)$_2$ | H | 0.5 | — | 0 | 10 | 0 | 5 | — | 5 | 10 |
|  |  |  | 2.0 | 0 | 0 | — | 0 | 10 | 20 | 3 | — |
|  |  |  | 4.0 | 0 | 5 | — | 20 | — | — | — | — |
| CH$_2$—O—CH$_3$ | —CH$_2$—CH$_2$Cl | H | 0.5 | — | 0 | 10 | 0 | 0 | — | 5 | 10 |
|  |  |  | 2.0 | 5 | 5 | — | 20 | 15 | 10 | 3 | — |
|  |  |  | 4.0 | 20 | 10 | — | 20 | — | — | — | — |
| CH$_2$—O—CH$_3$ | C$_3$H$_7$i | H | 0.5 | — | 0 | — | 25[++] | 10 | — | 0 | 10 |
|  |  | Br(6) | 2.0 | 0 | 0 | — | 25 | 20 | 15 | 3 | — |
|  |  |  | 4.0 | 0 | 10 | — | 30 | — | — | — | — |
| CH$_2$OH | C$_3$H$_7$i | H | 1.0 | 30 | 0 | 90 | 10 | 0 | — | — | — |
|  |  |  | 2.0 | 50 | 0 | 98 | 10 | 10 | — | — | — |
|  |  |  | 4.0 | 65 | 0 | 100 | 50 | 40 | — | — | — |

+ = no damage
100 = complete destruction
— = no values
++ *Cyperus rotundus*
+++ 6,8-dichloro-

Table 4

Control of unwanted plants in rice (Oryza sativa) and Indian corn (Zea mays) - postemergence treatment Basic molecule

| Substituted in position | | | Application rate | % damage to test plants[+] | | | | | | | |
|---|---|---|---|---|---|---|---|---|---|---|---|
| 1 | 3 | 8 | kg/ha | Oryza Sat. | Zea mays | Amar. retr. | Ammann. cocc. | Cyper. diff. | Ludw. pros. | Monoch. vagin. | Stell. med. |
| CH$_3$—CH(—O—C$_2$H$_5$)<br>prior art | C$_3$H$_7$i | H | 1.0 | 8 | 10 | 23 | 55 | 50 | — | 80 | 97 |
| | | | 2.0 | 8 | 17 | 38 | 64 | 78 | — | 90 | 97 |
| | | | 4.0 | 14 | — | 62 | 78 | 82 | — | 90 | 95 |
| CH$_3$—CH(—O—CH$_3$)<br>prior art | C$_3$H$_7$i | H | 1.0 | 5 | 10 | 20 | 57 | 30 | — | 50 | 100 |
| | | | 2.0 | 7 | 18 | 30 | 48 | 70 | — | 50 | 100 |
| | | | 4.0 | 7 | 22 | 62 | 67 | 70 | — | 50 | — |
| H<br>prior art | C$_3$H$_7$i | H | 1.0 | 0 | 7 | 48 | 80 | 67 | 50 | 80 | 100 |
| | | | 2.0 | 1 | 12 | 55 | 91 | 77 | 62 | 80 | 100 |
| | | | 4.0 | 2 | 13 | 82 | 97 | 89 | 87 | 90 | — |
| CH$_2$—O—CH$_3$ | C$_3$H$_7$i | H | 1.0 | 0 | 11 | 68 | 88 | 59 | 44 | 90 | 100 |
| | | | 2.0 | 1 | 15 | 76 | 92 | 80 | 73 | 90 | 100 |
| | | | 4.0 | 3 | 20 | 77 | 97 | 88 | — | 90 | — |
| CH$_2$—O—CH$_3$ | —CH$_2$—CH$_2$Cl | H | 1.0 | 5 | 5 | 10 | 10 | 0 | — | — | — |
| | | | 2.0 | 15 | 10 | 10 | 20 | 5 | — | — | — |
| | | | 4.0 | 22 | 15 | — | — | 5 | — | — | — |
| CH$_2$—O—CH$_3$ | CH$_3$—CH(—C$_2$H$_5$) | H | 1.0 | 0 | 15 | 20 | 77 | 27 | 7 | — | 95 |
| | | | 2.0 | 0 | 15 | 20 | 95 | 37 | 7 | — | 100 |
| | | | 4.0 | 0 | 20 | — | — | 55 | — | — | — |
| CH$_2$OH | C$_3$H$_7$i | H | 1.0 | 0 | 0 | 50 | 100 | — | — | — | 82 |
| | | | 2.0 | 0 | 0 | 50 | 100 | — | — | — | 95 |
| | | | 4.0 | 0 | 0 | 90 | 100 | — | — | — | 100 |

[+] 0 – 100 scale as in Table 3

Table 5

Selective weed control in carrots (Daucus carota) and sunflowers (Helianthus annuus) - postemergence treatment Basic molecule

| Substituted in position | | | | Application rate | % damage to test plants[+] | | | | | |
|---|---|---|---|---|---|---|---|---|---|---|
| 1 | 3 | 6 | 8 | kg/ha | Daucus carota | Helianth. annuus | Tritic. aestiv. | Chenop. album | Port. olerac. | Sinapis[++] alba |
| CH$_3$—CH(—O—C$_2$H$_5$)<br>prior art | C$_3$H$_7$i | H | H | 1.0 | — | 100 | 0 | 100 | — | 100 |
| | | | | 2.0 | — | 100 | 0 | 100 | — | 100 |
| | | | | 4.0 | — | 100 | 0 | 100 | — | 100 |
| CH$_3$—CH(—O—CH$_3$)<br>prior art | C$_3$H$_7$i | H | H | 1.0 | — | 100 | 0 | 98 | — | 100 |
| | | | | 2.0 | — | 100 | 0 | 100 | — | 100 |
| | | | | 4.0 | — | 100 | 0 | 100 | — | — |
| H<br>prior art | C$_3$H$_7$i | H | H | 1.0 | 100 | 100 | 0 | 76 | 60 | 90 |
| | | | | 2.0 | 100 | 100 | 0 | 88 | 60 | 95 |
| | | | | 4.0 | 100 | 100 | 0 | 100 | — | 100 |
| H<br>prior art | C$_3$H$_7$i | H | CH$_3$ | 1.0 | 100 | 100 | 0 | 80 | 40 | 100 |
| | | | | 2.0 | 100 | 100 | 0 | 100 | 40 | 100 |
| | | | | 4.0 | 100 | 100 | 0 | — | — | — |
| CH$_2$—O—CH$_3$<br>prior art | C$_3$H$_7$i | H | H | 1.0 | 17 | 9 | 0 | 72 | 95 | 87 |
| | | | | 2.0 | 30 | 18 | 0 | 90 | 95 | 97 |
| | | | | 4.0 | 52 | 47 | 0 | 100 | — | — |

Table 5-continued
Selective weed control in carrots (*Daucus carota*) and sunflowers (*Helianthus annuus*) - postemergence treatment Basic molecule

[Structure: benzothiadiazine-dioxide ring system with positions labeled 1 (N), 2 (SO$_2$), 3 (N), 4 (O), 5, 6, 7, 8]

| Substituted in position 1 | 3 | 6 | 8 | Application rate kg/ha | % damage to test plants[+] Daucus carota | Helianth. annuus | Tritic. aestiv. | Chenop. album | Port. olerac. | Sinapis[++] alba |
|---|---|---|---|---|---|---|---|---|---|---|
| CH$_2$—O—C$_2$H$_5$ | C$_3$H$_7$i | H | H | 1.0 | 75 | 30 | 0 | 100 | — | 85 |
|  |  |  |  | 2.0 | — | 85 | 0 | 100 | — | 100 |
|  |  |  |  | 4.0 | — | — | 0 | 100 | — | 100 |
| CH$_2$—O—C$_3$H$_7$i | C$_3$H$_7$i | H | H | 1.0 | 100 | 100 | 0 | 100 | — | 100 |
|  |  |  |  | 2.0 | — | 100 | 0 | 100 | — | 100 |
|  |  |  |  | 4.0 | — | 100 | 0 | — | — | — |
| CH$_2$—O—C$_3$H$_7$n | C$_3$H$_7$i | H | H | 1.0 | 90 | 60 | 0 | 100 | — | 100 |
|  |  |  |  | 2.0 | — | 80 | 0 | 100 | — | 100 |
|  |  |  |  | 4.0 | — | 100 | 0 | — | — | — |
| CH$_2$—O—CH$_3$ | C$_3$H$_7$i | Br | Br | 1.0 | 0 | 0 | 0 | 0 | — | 10 |
|  |  |  |  | 2.0 | 0 | 0 | 0 | — | — | 25 |
|  |  |  |  | 3.0 | — | — | 0 | — | — | 80 |
| CH$_2$—O—CH$_3$ | CH$_3$—CH—C$_2$H$_5$ | H | H | 1.0 | 10 | 10 | 0 | 0 | — | 57 |
|  |  |  |  | 2.0 |  |  |  |  |  |  |
|  |  |  |  | 3.0 | — | — | 0 | 13 | — | 80 |
|  |  |  |  | 4.0 | 10 | 10 | 0 | — | — | — |
| CH$_2$—O—C$_4$H$_9$n | C$_3$H$_7$i | H | H | 3.0 | — | — | 0 | — | — | 80 |
| CH$_2$—O—CH$_2$—CH(CH$_3$)$_2$ | C$_3$H$_7$i | H | H | 3.0 | — | — | 0 | — | — | 80 |
| CH$_2$—O—C(CH$_3$)$_3$ | C$_3$H$_7$i | H | H | 3.0 | — | — | 0 | — | — | 80 |
| CH$_2$—O—CH$_2$—CH=CH$_2$ | C$_3$H$_7$i | H | H | 3.0 | — | — | 0 | — | — | 80 |
| CH$_2$—O—CH$_2$—C≡CH | C$_3$H$_7$i | H | H | 3.0 | — | — | 0 | — | — | 80 |
| CH$_2$—O—C$_2$H$_4$—O—CH$_3$ | C$_3$H$_7$i | H | H | 3.0 | — | — | 0 | — | — | 80 |
| CH$_2$—O—⟨H⟩ (phenyl) | C$_3$H$_7$i | H | H | 3.0 | — | — | 0 | — | — | 80 |
| CH$_2$—O—(CH$_2$)$_4$CH$_3$ | C$_3$H$_7$i | H | H | 3.0 | — | — | 0 | — | — | 80 |
| CH$_2$—O—CH$_2$CH$_2$Cl | C$_3$H$_7$i | H | H | 3.0 | — | — | 0 | — | — | 60 |
| CH$_2$—O—CH(CH$_3$)(C$_2$H$_5$) | C$_3$H$_7$i | H | H | 3.0 | — | — | 0 | — | — | 80 |
| CH$_2$—O—CH$_3$ | CH$_3$—CH—CH$_2$Cl | H | H | 3.0 | — | — | 0 | — | — | 80 |
| CH$_2$—O—CH$_2$—CH=CH—CH$_3$ | C$_3$H$_7$i | H | H | 3.0 | — | — | 0 | — | — | 100 |
| CH$_2$—O—CH$_2$—CH$_2$—C(O)—CH$_3$ | C$_3$H$_7$i | H | H | 3.0 | — | — | 0 | — | — | 100 |

[+]0 - 100 scale as in previous tables
[++]*Sinapis alba*, frequently grown as crop plant, here as indicator of the biological action

Table 6
Influence of a non-phytotoxic oil on the herbicidal action and selectivity of 1-methoxymethyl-3-isopropyl-2,1,3-benzothiadiazin-(4)-one-2,2-dioxide- postemergence treatment Basic molecule

[Structure: benzothiadiazine-dioxide ring system with positions labeled 1 (N), 2 (SO$_2$), 3 (N), 4 (O), 5, 6, 7, 8]

| Substituted in position 1 | 3 | Application rate kg/ha | Oil additive[+] | % damage to test plants[++] Glyc. max | Gossyp. hirs. | Oryza sat. | Amar. retr. | Cyper. escul. | Sesban. exalt. | Sida spin. | Xanth. pennsyl. |
|---|---|---|---|---|---|---|---|---|---|---|---|
| H | C$_3$H$_7$i | 0.25 |  | — | — | — | 5 | — | 5 | 71 | 63 |
|  |  | 0.5 |  | 0 | — | 0 | 5 | 48 | 0 | 75 | 68 |
| prior art |  | 1.0 |  | 0 | 60 | 0 | 10 | 52 | 18 | 90 | — |
|  |  | 2.0 |  | 0 | 81 | 0 | 10 | 58 | 32 | 97 | — |

Table 6-continued

Influence of a non-phytotoxic oil on the herbicidal action and selectivity of 1-methoxymethyl-3-isopropyl-2,1,3-benzothiadiazin-(4)-one-2,2-dioxide-postemergence treatment Basic molecule

| Substituted in position 1 | 3 | Application rate kg/ha | Oil additive[+] | % damage to test plants[++] | | | | | | | |
|---|---|---|---|---|---|---|---|---|---|---|---|
| | | | | Glyc. max | Gossyp. hirs. | Oryza sat. | Amar. retr. | Cyper. escul. | Sesban. exalt. | Sida spin. | Xanth. pennsyl. |
| H prior art | $C_3H_7i$ | 4.0 | | 10 | 84 | 0 | — | 75 | — | — | — |
| | | 0.25 | +* | — | — | — | 5 | — | 40 | 86 | 82 |
| | | 0.5 | + | 7 | — | 21 | 5 | 67 | 40 | 80 | 82 |
| | | 1.0 | + | 12 | 77 | 27 | 10 | 73 | 78 | 92 | — |
| | | 2.0 | + | 15 | 80 | 31 | 20 | 75 | 96 | 97 | — |
| | | 4.0 | + | 19 | 92 | 34 | — | 92 | — | — | — |
| $CH_2$—O—$CH_3$ | $C_3H_7i$ | 0.25 | | — | — | — | 15 | — | 0 | 68 | 37 |
| | | 0.5 | | 0 | — | 0 | 20 | 13 | 0 | 82 | 62 |
| | | 1.0 | | 0 | 0 | 0 | 95 | 43 | 30 | 92 | — |
| | | 2.0 | | 2 | 6 | 2 | 95 | 87 | 64 | 96 | — |
| | | 4.0 | | 10 | 14 | 5 | — | 92 | — | — | — |
| $CH_2$—O—$CH_3$ | $C_3H_7i$ | 0.25 | +* | — | — | — | 32 | — | 0 | 86 | 67 |
| | | 0.5 | + | 7 | — | 4 | 25 | 54 | 40 | 92 | 67 |
| | | 1.0 | + | 12 | 0 | 5 | 95 | 70 | 89 | 97 | — |
| | | 2.0 | + | 17 | 0 | 5 | 95 | 84 | 89 | 97 | — |
| | | 4.0 | + | 22 | 0 | 5 | — | 95 | — | — | — |

*Amount added = $\frac{1}{20}$ of volume of spray liquor

[++] 0 – 100 scale as in previous tables

Table 7

Action on some test plants when applied preemergence

Basic molecule

| Substituted in position 1 | 3 | 6 | Application rate kg/ha | % damage to test plants[+] | | | | |
|---|---|---|---|---|---|---|---|---|
| | | | | Avena sativa | Beta vulg. | Daucus carota | Lolium multifl. | Sinapis alba |
| H prior art | $C_3H_7i$ | H | 2.0 | — | 99 | 100 | — | — |
| | | | 3.0 | 0 | — | — | 0 | 80 |
| | | | 4.0 | — | 99 | 100 | — | — |
| $CH_2$—O—$CH_3$ | $C_3H_7i$ | H | 2.0 | — | 100 | 45 | — | — |
| | | | 3.0 | 0 | — | — | 0 | 80 |
| | | | 4.0 | — | 100 | 60 | — | — |
| $CH_2$—O—$C_2H_5$ | $C_3H_7i$ | H | 2.0 | — | 75 | 100 | — | — |
| | | | 3.0 | 0 | — | — | 0 | 80 |
| | | | 4.0 | — | — | 100 | — | — |
| $CH_2$—O—$C_3H_7i$ | $C_3H_7i$ | H | 2.0 | — | 100 | 100 | — | — |
| | | | 3.0 | 0 | — | — | 0 | 80 |
| | | | 4.0 | — | 100 | 100 | — | — |
| $CH_2$—O—$C_3H_7n$ | $C_3H_7i$ | H | 2.0 | — | 100 | 100 | — | — |
| | | | 3.0 | 0 | — | — | 0 | 80 |
| | | | 4.0 | — | 100 | 100 | — | — |
| $CH_2$—O—$CH_3$ | $C_2H_5$ | H | 2.0 | — | 97 | 45 | — | — |
| | | | 3.0 | 0 | — | — | 0 | 80 |
| | | | 4.0 | — | 100 | 55 | — | — |
| $CH_2$—O—$CH_3$ | $C_3H_7n$ | H | 2.0 | — | 67 | 45 | — | — |
| | | | 3.0 | 0 | — | — | 0 | 60 |
| | | | 4.0 | — | 67 | 55 | — | — |
| $CH_2$—O—$CH_3$ | —$CH(C_2H_5)$ | H | 2.0 | — | 0 | 45 | — | — |
| | | | 3.0 | 0 | — | — | 0 | 40 |
| | | | 4.0 | — | 0 | — | — | — |
| $CH_2$—O—$CH_3$ | $CH_2$—$CH_2Cl$ | H | 2.0 | — | 65 | 5 | — | — |
| | | | 3.0 | 0 | — | — | 0 | 0 |
| | | | 4.0 | — | 87 | 10 | — | — |
| $CH_2$—O—$CH_3$ | $C_3H_7i$ | Br | 2.0 | — | 0 | — | — | — |
| | | | 3.0 | 0 | — | — | 0 | 0 |
| | | | 4.0 | — | 0 | — | — | — |

Table 7-continued

Action on some test plants when applied preemergence

Basic molecule (benzothiadiazinone structure with positions 1, 2(SO$_2$), 3(N), 4(O), 5, 6, 7, 8)

| Substituted in position 1 | 3 | 6 | Application rate kg/ha | % damage to test plants[+] Avena sativa | Beta vulg. | Daucus carota | Lolium multifl. | Sinapis alba |
|---|---|---|---|---|---|---|---|---|
| CH$_2$—O—CH$_3$ | CH$_3$—CH—C$_2$H$_5$ | H | 2.0 | — | — | 15 | — | — |
|  |  |  | 3.0 | 0 | — | — | 0 | 80 |
|  |  |  | 4.0 | — | — | 20 | — | — |

[+] 0 – 100 scale as in previous tables

Table 8

Improved weed control in various crops by mixing active ingredients - postemergence treatment Basic molecule (benzothiadiazinone structure with positions 1, 2(SO$_2$), 3(N), 4(O), 5, 6, 7, 8)

| Substituted in position 1 | 3 | 8 | Appli-cation rate kg/ha | % damage to test plants[+] Gossyp. hirs. | Glyc. max | Mentha piper. | Oryza sat. | Amar. retr. | Cyper. diff. | Ipom. spp. | Sesban. exalt. | Sida spin. |
|---|---|---|---|---|---|---|---|---|---|---|---|---|
| A  H prior art | C$_3$H$_7$i | H | 0.25 | — | — | 0 | — | 50 | — | 32 | 0 | 92 |
|  |  |  | 0.5 | 77 | 0 | 0 | 0 | 60 | 55 | 35 | 0 | 92 |
|  |  |  | 1.0 | 95 | 0 | 0 | 0 | 100 | 70 | 50 | 0 | 97 |
|  |  |  | 2.0 | 95 | 0 | 0 | 0 | 100 | 75 | 62 | 12 | 97 |
|  |  |  | 4.0 | 95 | 0 | — | 0 | — | 85 | — | 20 | 95 |
| B  H | C$_3$H$_7$i | CH$_3$ | 0.25 | — | — | 0 | — | 35 | — | 20 | 0 | 20 |
|  |  |  | 0.5 | 15 | 0 | 0 | 0 | 40 | 65 | 25 | 10 | 25 |
|  |  |  | 1.0 | 25 | 0 | 0 | 0 | 60 | 65 | 25 | 57 | 57 |
|  |  |  | 2.0 | 30 | 0 | 0 | 0 | 100 | 70 | 33 | 95 | 90 |
|  |  |  | 4.0 | 60 | 0 | — | 0 | — | 70 | — | — | — |
| CH$_2$—O—CH$_3$ C | C$_3$H$_7$i | H | 0.25 | — | — | 0 | — | 90 | — | 35 | 17 | 100 |
|  |  |  | 0.5 | 2 | 0 | 0 | 0 | 100 | 50 | 45 | 22 | 97 |
|  |  |  | 1.0 | 0 | 0 | 0 | 0 | 100 | 55 | 60 | 60 | 97 |
|  |  |  | 2.0 | 12 | 0 | 0 | 0 | 100 | 67 | 73 | 77 | 97 |
|  |  |  | 4.0 | 25 | 0 | — | 0 | — | 82 | — | — | — |

| Mixture of compounds | Application rate kg/ha | % damage to test plants[+] Gossyp. hirs. | Glyc. max | Mentha piper. | Oryza sat. | Amar. retr. | Cyper. diff. | Ipom. spp. | Sesban. exalt. | Sida spin. |
|---|---|---|---|---|---|---|---|---|---|---|
| A + B | 0.125+0.125 | 10 | 0 | 0 | 0 | 10 | 65 | 22 | 10 | 97 |
|  | 0.25 +0.25 | 10 | 0 | 0 | 0 | 30 | 75 | 30 | 47 | 97 |
|  | 0.25 +0.75 | 50 | 0 | 0 | 0 | 100 | 77 | 35 | 42 | 97 |
|  | 0.5 +0.5 | 32 | 0 | 0 | 0 | 30 | 82 | 38 | 82 | 97 |
|  | 0.5 +1.0 | 27 | 0 | 0 | 0 | 80 | 75 | 40 | 67 | 97 |
|  | 0.5 +1.5 | 55 | 0 | 0 | 0 | 100 | 77 | 40 | 72 | 97 |
|  | 0.75 +0.25 | 75 | 0 | 0 | 0 | 65 | 70 | 40 | 47 | 97 |
|  | 1.0 +0.5 | 45 | 0 | 0 | 0 | 100 | 90 | 43 | 47 | 97 |
|  | 1.0 +1.0 | 50 | 0 | 0 | 0 | 80 | 90 | 50 | 82 | 97 |
|  | 1.0 +3.0 | 72 | 0 | 0 | 0 | 100 | 82 | 58 | 87 | 97 |
|  | 1.5 +0.5 | 77 | 0 | 0 | 0 | 95 | 77 | 48 | 47 | 97 |
|  | 2.0 +2.0 | 55 | 10 | 0 | 0 | 80 | 90 | 53 | 92 | 97 |
|  | 3.0 +1.0 | 95 | 0 | 0 | 0 | 95 | 90 | 67 | 72 | 97 |
| A + C | 0.125+0.125 | 20 | 0 | — | 0 | — | 57 | 20 | 20 | 45 |
|  | 0.25 +0.25 | 20 | 0 | — | 0 | — | 57 | 27 | 20 | 58 |
|  | 0.5 +0.5 | 50 | 0 | — | 0 | — | 80 | 50 | 20 | 78 |
|  | 1.0 +1.0 | 60 | 10 | — | 0 | — | 85 | 78 | 60 | 97 |
|  | 1.5 +1.5 | — | — | — | — | — | — | — | — | — |
| C + B | 0.125+0.125 | 15 | 0 | 0 | 0 | 100 | 70 | 40 | 25 | 62 |
|  | 0.25 +0.25 | 20 | 0 | 0 | 0 | 100 | 75 | 50 | 47 | 87 |
|  | 0.25 +0.75 | 17 | 0 | 0 | 0 | 100 | — | 53 | 72 | 97 |
|  | 0.5 +0.5 | 20 | 0 | 0 | 0 | 100 | 85 | 60 | 52 | 97 |
|  | 0.5 +1.0 | 25 | 0 | 0 | 0 | 100 | 72 | 58 | 57 | 97 |
|  | 0.5 +1.5 | 52 | 0 | 0 | 0 | 100 | 62 | 62 | 95 | 97 |
|  | 0.75 +0.25 | 17 | 0 | 0 | 0 | 100 | 70 | 70 | 57 | 97 |
|  | 1.0 +0.5 | 10 | 0 | 0 | 0 | 100 | 70 | 77 | 72 | 97 |
|  | 1.0 +1.0 | 37 | 0 | 0 | 0 | 100 | 87 | 73 | 77 | 97 |
|  | 1.0 +3.0 | 95 | 0 | 0 | 0 | 100 | 62 | 72 | 95 | 97 |

Table 8-continued
Improved weed control in various crops by mixing active ingredients - postemergence treatment Basic molecule

| 1.5 +0.5 | 32 | 0 | 0 | 0 | 100 | 80 | 73 | 95 | 97 |
| 2.0 +2.0 | 87 | 0 | 0 | 0 | 100 | 90 | 78 | 95 | 97 |
| 3.0 +1.0 | 45 | 0 | 0 | 0 | 100 | 80 | 73 | 95 | 97 |

+ 0 – 100 scale, as in previous tables

EXAMPLE 14

147 parts by weight of 1-methoxymethyl-3-isopropyl-2,1,3-benzothiadiazin-(4)-one-2,2-dioxide and 37 parts by weight of phosphorus pentasulfide are refluxed for 5 hours in 300 parts by volume of toluene. After cooling, the solution is filtered, diluted with 2,000 parts by volume of diethyl ether, washed with 1,000 parts by volume of 3% (wt%) caustic soda solution and 1,000 parts by volume of water, dried over sodium sulfate and concentrated in vacuo. The residue obtained crystallizes after a short period of time, and weights 149 parts by weight. After recrystallization from methylene chloride there is obtained 138 parts by weight of the compound

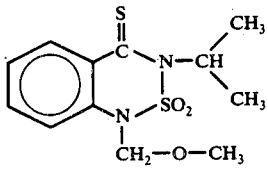

Melting point: 149° C

Application may be effected for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used; in any case they should ensure a fine distribution of the active ingredient.

For the preparation of solutions, emulsions, pastes and oil dispersions to be sprayed direct, mineral oil fractions of medium to high boiling point, such as kerosene or diesel oil, further coal-tar oils, etc. and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples or surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ether, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenol polyglycol ethers, alkylaryl polyester alcohols, isotridecyl alcohols, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite wate liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, Attaclay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations contain from 0.1 to 95, and preferably 0.5 to 90% by weight of active ingredient.

There may be added to the compositions or individual active ingredients (if desired, immediately before use (tankmix)) oils of various types, wetting agents or adherents, herbicides, fungicides, nematocides, insecticides, bactericides, trace elements, fertilizers, actifoams (e.g., silicones), growth regulators, antidotes and other herbicidally effective compounds such as
- substituted alkylsulfonylglycolic amides and imides
- substituted alkylaminosulfonylglycolic amides and imides
- substituted acetanilidoalkyl sulfites
- substituted anilines
- substituted azides
- substituted aryloxycarboxylic acids and aryloxythiocarboxylic acids and salts, esters and amides thereof,
- substituted alkanols, alkenols
- substituted ethers
- substituted arsonic acids and arsenic acids and salts, esters and amides thereof
- substituted benzene sulfonamides
- substituted benzimidazoles
- substituted benzisothiazoles
- substituted dihydrobenzofuranyl alkylamino sulfonates
- substituted benzothiadiazinone dioxides
- substituted benzoxazines
- substituted benzoxazinones
- substituted benzoxaline thiones
- substituted benzothiadiazoles
- substituted benzothiazolinyl alkyl carboxylic acids and salts, esters and amides thereof
- substituted biurets
- substituted quinolines
- substituted carbamates
- substituted aliphatic or cycloaliphatic carboxylic acids and thiocarboxylic acids and their salts, esters and amides
- substituted aromatic carboxylic acids and thiocarboxylic acids and their salts, esters and amides
- substituted carbamoylalkylthiol- or -dithiophosphates
- substituted quinazolines
- substituted cycloalkylamidocarbothiolic acids and their salts, esters and amides
- substituted cycloalkylcarbonamidothiazoles
- substituted dicarboxylic acids and their salts, esters and amides
- substituted dihydrobenzofuranyl sulfonates
- substituted dihydropyran diones
- substituted disulfides
- substituted dioxanes
- substituted dipyridylium salts
- substituted dithiocarbamates
- substituted dithiophosphoric acids and their salts, esters and amides
- substituted fluorenecarboxylic acids and their salts, esters and amides
- substituted ureas
- substituted hexahydro-1H-carbothioates
- hexahydro-1H-carbothioates
- substituted hydantoins
- substituted hydrazides
- substituted hydrazonium salts
- substituted hydrofuranones
- substituted cyclohexane diones
- substituted isoxazole pyrimidones
- substituted imidazoles
- substituted imidazolidinedione carboxamides
- substituted isothiazole pyrimidones
- substituted ketones
- substituted naphthoquinones
- substituted naphthalic anhydrides
- substituted aliphatic nitriles
- substituted aromatic nitriles
- substituted oxadiazoles
- substituted oxadiazinones
- substituted oxadiazolines
- substituted oxadiazolidine diones
- substituted oxazolidines
- substituted oxadiazine diones
- substituted oxazole pyrimidinones
- substituted phenols and their salts and esters
- substituted phosphonic acids and their salts, esters and amides
- substituted phosphonium chlorides
- substituted phosphonalkyl glycines
- substituted phosphites
- substituted phosphoric acids and their salts, esters and amides
- substituted piperidines
- substituted pyrazoles
- substituted pyrazole alkylcarboxylic acids and their salts, esters and amides
- substituted pyrazolium salts
- substituted pyrazolium alkyl sulfates
- substituted pyridazines
- substituted pyridazones
- substituted pyridine carboxylic acids and their salts, esters and amides
- substituted pyridines
- substituted pyridine carboxylates
- substituted pyridinones
- substituted pyrimidines
- substituted pyrimidones
- substituted pyrrolidone carboxylic acid and its salts, esters and amides
- substituted pyrrolidines
- substituted pyrrolidones
- substituted arylsulfonic acids and their salts, esters and amides
- substituted sulfamates
- substituted styrenes
- substituted sulfonyl toluidides
- substituted tetrahydrooxadiazine diones
- substituted tetrahydroxadiazole diones
- substituted tetrahydromethanoindenes
- substituted tetrahydroxadiazole thiones
- substituted tetrahydrothiadiazine thiones
- substituted tetrahydrothiadiazole diones
- substituted aromatic thiocarbonylamides
- substituted thiobenzamides
- substituted thiocarboxylic acids and their salts, esters and amides
- substituted thiol carbamates
- substituted thioureas
- substituted thiophosphoric acids and their salts, esters and amides
- substituted triazines
- substituted triazinones
- substituted triazoles
- substituted uracils
- substituted uretidine diones chlorates, and
- substituted azetidine carbothioates.

The last-mentioned herbicidal compounds may also be applied before or after the active ingredients or compositions thereof according to the invention.

These agents may be added to the herbicides according to the invention in a ratio by weight of from 1:10 to 10:1. The same applies to oils, wetting agents and adherents, fungicides, nematocides, insecticides, bactericides, antidotes and growth regulators.

We claim:

1. A compound of the formula

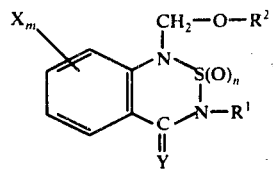

wherein $R^1$ is hydrogen, alkyl of from 1 to 7 carbon atoms, lower haloalkyl, cycloalkyl of from 3 to 7 carbon atoms, lower alkenyl, lower alkynyl, lower alkoxyalkyl, lower alkylmercapto-alkyl, phenyl, halogen-substituted phenyl or methyl-substituted phenyl; $R^2$ is hydrogen, alkyl of from 1 to 20 carbon atoms, lower haloalkyl, cycloalkyl of from 3 to 7 carbon atoms, lower alkenyl, lower alkynyl, lower haloalkenyl, lower haloalkynyl, lower alkoxyalkyl, lower alkylmercaptoalkyl, lower alkylcarbamoylalkyl, lower dialkylcarbamoylalkyl, lower alkoxycarboalkyl, lower alkoxycarboalkenyl, lower alkylketone or benzyl, with the proviso that $R^1$ and $R^2$ cannot simultaneously denote hydrogen; and each X is independently halogen, $NO_2$, lower alkyl, halo lower alkyl, cycloalkyl of from 3 to 7 carbon atoms, phenyl, halogen-substituted phenyl, methyl-substituted phenyl,

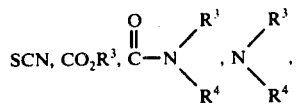

$NH_2$, $Y''R^4$, $SO_2R^3$, $SO_2OR^3$,

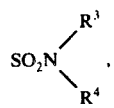

$CCl_3$, $CF_3$,

or $Y'CF_2C(Z)_3$, $m$ denotes one of the integers 0, 1, 2, 3 and 4, and n denotes one of the integers 1 and 2, $R^3$ denoting lower alkyl, $R^4$ denoting lower alkyl or hydrogen, each Y, Y' and Y'' independently denoting oxygen or sulfur, and each Z independently denoting hydrogen, fluoro, bromo and chloro.

2. A process for controlling the growth of unwanted plants, wherein the soil or the plants are treated with a compound of the formula

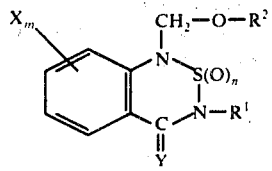

where $R^1$ is hydrogen, alkyl of from 1 to 7 carbon atoms, lower haloalkyl, cycloalkyl of from 3 to 7 carbon atoms, lower alkenyl, lower alkynyl, lower alkoxyalkyl, lower alkylmercaptoalkyl, phenyl, halogen-substituted phenyl or methyl-substituted phenyl;

$R^2$ is hydrogen, alkyl of from 1 to 20 carbon atoms, lower haloalkyl, cycloalkyl of from 3 to 7 carbon atoms, lower alkenyl, lower alkynyl, lower haloalkenyl, lower haloalkynyl, lower alkoxyalkyl, lower alkylmercaptoalkyl, lower alkylcarbamoylalkyl, lower dialkylcarbamoylalkyl, lower alkoxycarboalkyl, lower alkoxycarboalkenyl, lower alkylketone or benzyl, with the proviso that $R^1$ and $R^2$ cannot simultaneously denote hydrogen; and each X is independently halogen, $NO_2$, lower alkyl, halo lower alkyl, cycloalkyl of from 3 to 7 carbon atoms, phenyl halogen substituted phenyl, methyl-substituted phenyl, SCN, $CO_2R^3$,

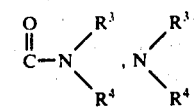

$NH_2$, $Y''R^4$, $SO_2R^3$, $SO_2OR^3$,

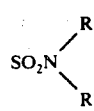

$CCl_3$, $CF_3$,

or $Y'CF_2C(Z)_3$, $m$ denotes one of the integers 0, 1, 2, 3 and 4, and $n$ denotes one of the integers 1 and 2, $R^3$ denoting lower alkyl, $R^4$ denoting lower alkyl or hydrogen, each Y, Y' and Y''' independently denoting oxygen or sulfur, and each Z independently denoting hydrogen, fluoro, bromo or chloro.

3. A substituted 2,1,3-benzothiadiazine compound selected from the group consisting of 1-methoxymethyl-3-ethyl-2,1,3-benzothiadiazin-(4)-one-2,2-dioxide, 1-methoxymethyl-3-n-propyl-2,1,3-benzothiadiazin-(4)-one-2,2-dioxide, 1-methoxymethyl-3-(3'-pentyl)-2,1,3-benzothiadiazin-(4)-one-2,2-dioxide, 1-methoxymethyl-3-isopropyl-6,8-dibromo-2,1,3-benzothiadiazin-(4)-one-2,2-dioxide, 1-methoxymethyl-3-β-chloroethyl-2,1,3-benzothiadiazine-(4)-one-2,2-dioxide, 1-methoxymethyl-3-isobutyl-2,1,3-benzothiadiazin-(4)-one-2,2-dioxide, 1-methoxymethyl-3-isopropyl-6-bromo-2,1,3-benzothiadiazin-(4)-one-2,2-dioxide, 1-methoxymethyl-3-β-chloroisopropyl-2,1,3-benzothiadiazin-(4)-one-2,2-dioxide, 1-hydroxymethyl-3-isopropyl-1,2,3-benzothiadiazin-(4)-one-2,2-dioxide, 1-methoxymethyl-3-isopropyl-6,8-dinitro-2,1,3-benzothiadiazin-(4)-one-2,2-dioxide and 1-methoxymethyl-3-isopropyl-2,1,3-benzothiadiazin-(4)-one-2,2-dioxide.

* * * * *